United States Patent
Khalaj

(10) Patent No.: US 9,248,260 B2
(45) Date of Patent: *Feb. 2, 2016

(54) CATHETER STRAIN RELIEF CLIP

(71) Applicant: Avent, Inc., Alpharetta, GA (US)

(72) Inventor: Steve Saeed Khalaj, Laguna Hills, CA (US)

(73) Assignee: Avent, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/641,961

(22) Filed: Mar. 9, 2015

(65) Prior Publication Data

US 2015/0246207 A1   Sep. 3, 2015

Related U.S. Application Data

(63) Continuation of application No. 14/089,957, filed on Nov. 26, 2013, now Pat. No. 8,974,421.

(51) Int. Cl.
*A61M 25/02*   (2006.01)

(52) U.S. Cl.
CPC ......... *A61M 25/02* (2013.01); *A61M 2025/024* (2013.01); *A61M 2025/028* (2013.01); *A61M 2025/0266* (2013.01)

(58) Field of Classification Search
CPC .............. A61M 2025/01; A61M 2025/02; A61M 2025/0206; A61M 2025/0213; A61M 2025/024; A61M 2025/026; A61M 2025/0293; A61M 16/0683; A61M 25/01; A61M 25/02
USPC ............ 604/165.03, 174, 178–179, 180, 181; 128/DIG. 26; 248/200, 217.2, 217.3, 248/205.3
See application file for complete search history.

(56) References Cited

U.S. PATENT DOCUMENTS

| | | |
|---|---|---|
| 5,147,320 A | 9/1992 | Reynolds et al. |
| 5,800,402 A | 9/1998 | Bierman |
| 5,810,781 A | 9/1998 | Bierman |
| 6,074,379 A | 6/2000 | Prichard |
| 6,134,754 A * | 10/2000 | Hansson ............ A61B 19/0256 24/115 R |
| 7,799,001 B2 | 9/2010 | Bierman |
| 8,974,421 B1 * | 3/2015 | Khalaj .................. A61M 25/02 604/174 |
| 2002/0150858 A1 | 10/2002 | Jordan et al. |
| 2006/0195117 A1 | 8/2006 | Rucker et al. |
| 2009/0043260 A1 | 2/2009 | Bierman |
| 2010/0006738 A1 | 1/2010 | Teirstein |

(Continued)

FOREIGN PATENT DOCUMENTS

| | | |
|---|---|---|
| EP | 0 574 961 A1 | 12/1993 |
| EP | 0 931 560 A1 | 7/1999 |
| WO | WO 99/56802 A1 | 11/1999 |

(Continued)

OTHER PUBLICATIONS

PCT Search Report, Feb. 10, 2015.

*Primary Examiner* — Theodore Stigell
*Assistant Examiner* — Amber Stiles
(74) *Attorney, Agent, or Firm* — Dority & Manning, P.A.

(57) ABSTRACT

A catheter strain relief clip includes a body having an upper surface, and a plurality of arm members extending upwardly from the upper surface. Each of the arm members defines an undercut region for receipt of a catheter. The arm members are disposed so as to define a bent path for a catheter threaded under each of the arm members from a first side to an opposite side of the body.

14 Claims, 3 Drawing Sheets

(56) References Cited

U.S. PATENT DOCUMENTS

2012/0123343 A1 5/2012 Aviles
2014/0066856 A1 3/2014 Peterson et al.

FOREIGN PATENT DOCUMENTS

| WO | WO 2009/137607 A1 | 11/2009 |
| WO | WO 2012/052717 A1 | 4/2012 |

* cited by examiner

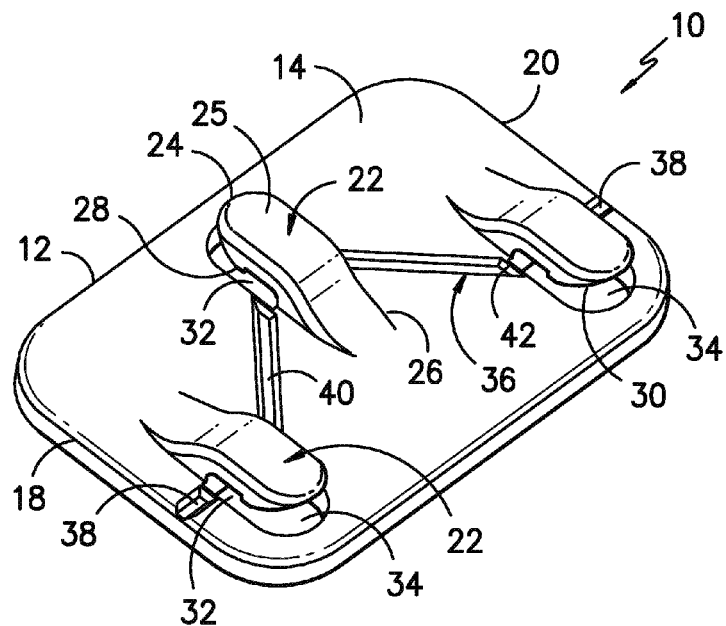
FIG. -1-
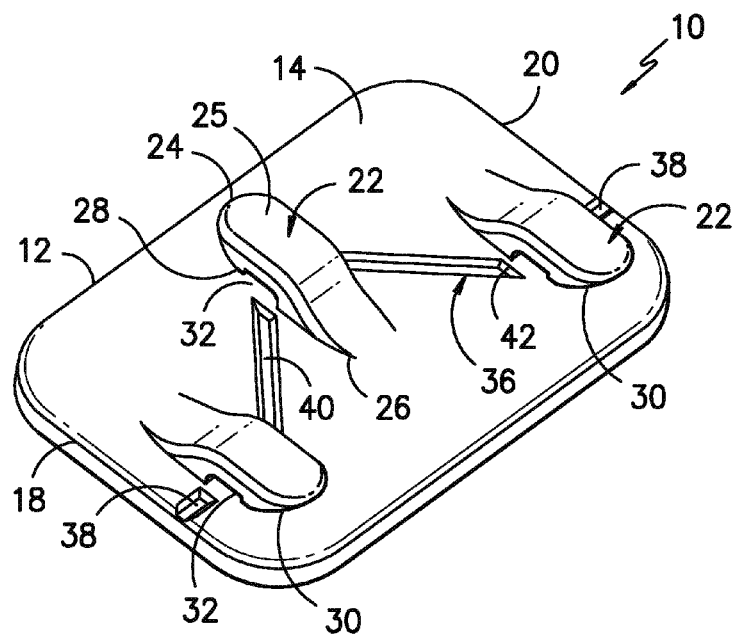
FIG. -2-

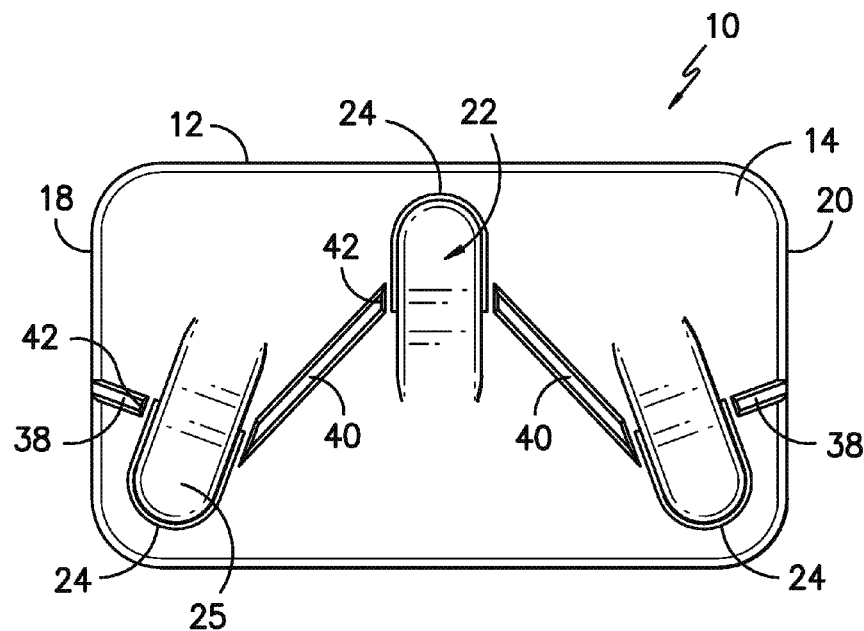
FIG. -3-
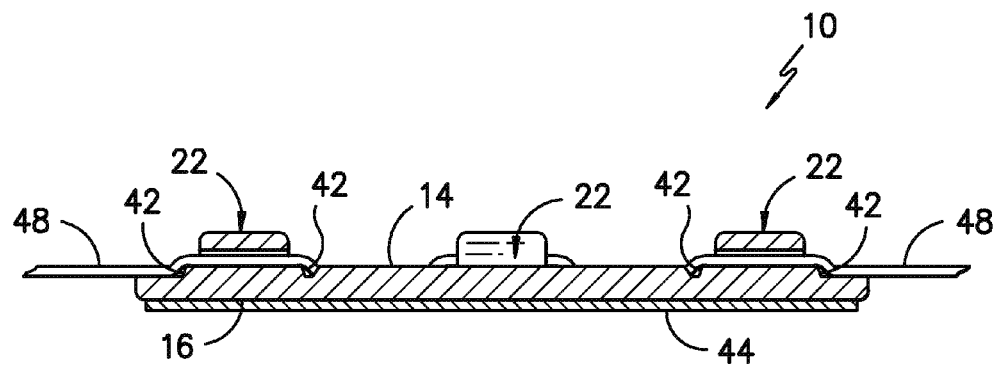
FIG. -4-

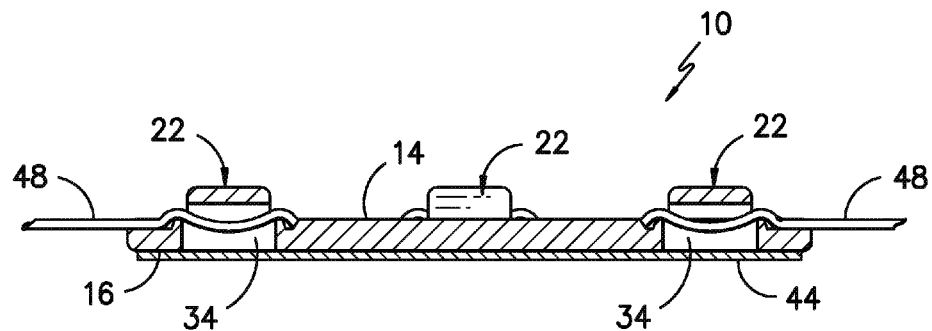
FIG. -5-
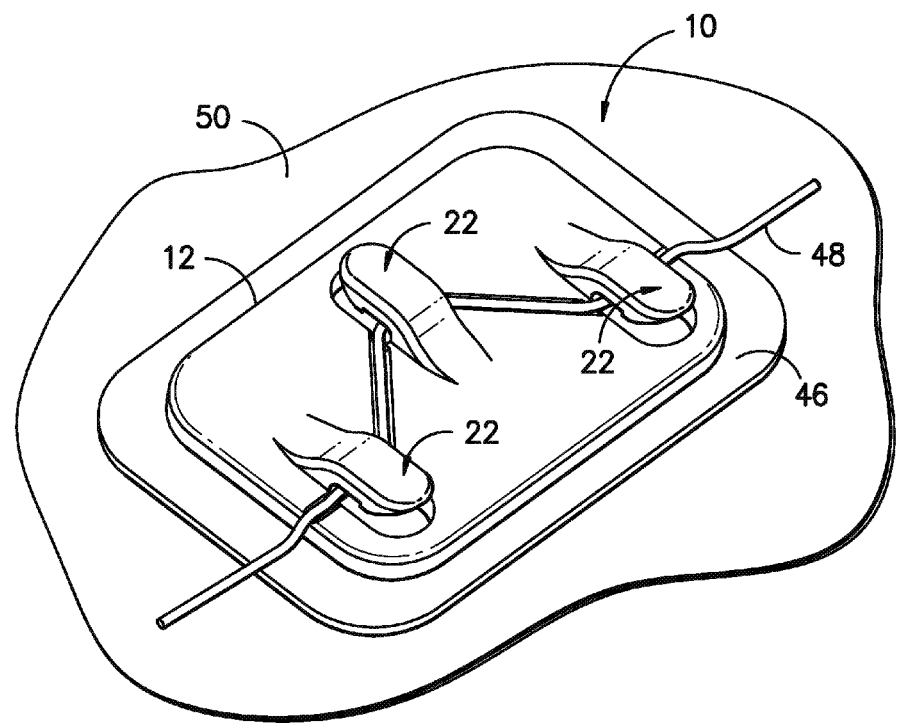
FIG. -6- ial, oval, square, and so forth. In a particular embodiment, the body has an overall rectangular shape. A plurality of arm members extend upwardly from the upper surface of the body, wherein each of the arm members defines an undercut region between a lower surface of the arm member and the plane of the upper surface of the body for receipt of a catheter under the respective arm member.

CATHETER STRAIN RELIEF CLIP

PRIORITY APPLICATION

The present Application is a Continuation Application of U.S. application Ser. No. 14/089,957, filed Nov. 26, 2013, issued as U.S. Pat. No. 8,974,421 on Mar. 10, 2015.

FIELD OF THE INVENTION

The present invention relates generally to the field of medical catheters, and more particularly to a clip device for securing a catheter at a target location on a patient.

BACKGROUND

The use of catheters to deliver or withdraw fluids from a patient for various medical procedures is well known. For example, U.S. Pat. No. 7,959,623 describes a pain management system that uses various embodiments of infusion catheters to deliver fluid medication from a pump, through tubing, to a wound site. With such systems, catheter connectors are typically used to connect the catheter to various devices, such as tubing, a fluid reservoir or other fluid delivery device, and so forth. In the system of the U.S. '623 patent, a conventional Toughy Borst connector is used to connect the distal end of a medical tube to the proximal end of the catheter.

In addition, it is also a common practice to utilize a "strain relief" device to prevent the catheter from kinking or otherwise collapsing when subjected to lateral bending forces, typically at or near the juncture of the catheter and the connector. These devices are generally designed to prevent bending forces from concentrating at this critical juncture by spreading the bending forces along an adequate length of the catheter tube displaced from the connector. For example, U.S. Pat. No. 6,074,379 describes a catheter strain relief device having an elongate body formed of an elastomeric material with a lumen defined therethrough and divided into proximal, central, and distal portions having varying diameters. The catheter tube is slid through the lumen. This device also includes suture wings that provide for suturing the device to a target location on the patient.

A conventional catheter strain relief device is the "Statlock™ Stabilization Device" from Bard Access Systems of Salt Lake City, Utah, USA. This device is particularly designed for securement of epidural catheters used for regional anesthesia and includes a retainer mounted on an adhesive anchor pad. The retainer defines a serpentine retention path through which the catheter is threaded, as well as a spot of adhesive over which the catheter runs (and in pressed into) to further secure the catheter.

The medical arts are thus continuously seeking new and improved devices for securing and relieving bending stresses in catheters at a target site, wherein such devices are reliable, relatively easy to use, and provide for quick insertion and release of the catheter. The present invention provides such a device.

SUMMARY OF THE INVENTION

Objects and advantages of the invention will be set forth in part in the following description, or may be obvious from the description, or may be learned through practice of the invention.

In certain aspects, the present invention relates to a catheter strain relief clip having a body with an upper surface. The body can have any conventional overall shape, such as circular, oval, square, and so forth. In a particular embodiment, the body has an overall rectangular shape. A plurality of arm members extend upwardly from the upper surface of the body, wherein each of the arm members defines an undercut region between a lower surface of the arm member and the plane of the upper surface of the body for receipt of a catheter under the respective arm member.

The arm members are provided in sufficient number and orientation on the upper surface so as to define a bent path for a catheter threaded under each of the arm members from a first side to a second side of the body, which may be the opposite side of the body. For example, in one embodiment, three or more arm members define a bent path wherein the catheter changes direction at least three times and runs along at least two angled segments from the first side to the opposite side of the body. The bent path may be serpentine, curved, segmented, or other shape.

In a particular embodiment, at least three of the arm members are provided, wherein the bent is defined to one side of an axis between the outermost arm members. In other words, the catheter enters the body at the first side, changes direction at each of the arm members, and exits the body at the opposite side in the same direction that it entered at the first side, wherein the intermediate arm members are all to one side of an axis between the outermost arm members. This embodiment may be desired to reduce the width of the body member while at the same time providing adequate retention and directional change of the catheter for strain relief purposes.

In a particular embodiment, all of the arm members are oriented parallel to each other on the upper surface of the body such that the change in direction of the bent path is due essentially solely to the offset of the arm members relative to each other. In another embodiment, at least two of the arm members are oriented at non-parallel angles to each other such that the change in direction of the bent path is also due to an angular skew between certain of the arm members. For example, the opposite outermost pair of the arm members may be oriented or skewed at a non-parallel angle (relative to each other or to an intermediate arm member) on the upper surface so as to increase the directional change of the bent path at the sides of the body, while intermediate arm members may be oriented parallel to each other.

The arm members may be resiliently configured on the body so as to flex for insertion and removal of the catheter from the undercut regions. In addition, a retention lip may be defined on an underside of the arm members to prevent inadvertent slippage of the catheter from under the arm member. The arm members may include an inclined face on the underside thereof extending from the lip to the free end of the arms to aid with sliding insertion of the catheter under the arm member.

In certain embodiments, a recess or hole is defined in the body member at each of the undercut regions, wherein a catheter disposed through the undercut regions can deflect vertically into the recess or hole.

In some embodiments, "grooves" may be defined in the upper surface of the body between each of the arm members, wherein the grooves define recessed channels or a change in elevation of one surface with respect to an adjacent surface (relative to the upper surface) for receipt of the catheter therein between the arm members. The grooves may be defined at their opposite ends by walls adjacent to the undercut regions, wherein each arm member is flanked by such delimiting walls. With this configuration, a catheter seated in the channels is deflected vertically by the walls at each of the undercut regions. In addition, where a recess or hole is defined in the body at the undercut regions, the catheter is deflected vertically downward into such recess or hole at the undercut regions. The cumulative effect of the vertical deflections is beneficial in retaining the catheter and relieving axial stresses, particularly if the catheter is subjected to a pulling force from only one direction The clip device may be provided with various adhesive means to retain the device at a target location on the patient. For example, in one embodiment the body comprises a flat underside with an adhesive provided directly thereon (and protected with a peel-off layer until use of the device). With an alternate embodiment, the body may be attached to an adhesive pad, which has an adhesive surface for securing the clip at a target location.

BRIEF DESCRIPTION OF THE DRAWINGS

FIG. 1 is a perspective view of an exemplary catheter clip in accordance with aspects of the invention;

FIG. 2 is a perspective view of an alternate embodiment of a catheter clip in accordance with aspects of the invention;

FIG. 3 is a top vies of yet another embodiment a catheter clip;

FIG. 4 is a side cut-away view of the catheter clip in the embodiment of FIG. 2;

FIG. 5 is a side cut-away view of the catheter clip in the embodiment of FIG. 1;

FIG. 6 is a perspective view of the catheter clip of FIG. 1 with an attachment pad and catheter.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site (e.g., the distal end of the connector is the end oriented towards a catheter insertion site), and "proximal" refers to the opposite direction (e.g., the proximal end of the catheter is inserted into the distal end of the connector).

FIG. 1 is a perspective view of an embodiment of a catheter strain relief clip 10 in accordance with aspects of the invention. The clip 10 is used for securing a catheter 48 (FIG. 6) at a target location on a patient, and is particularly useful as a strain relief and retaining device located distally to a catheter connector generally near the insertion site in the patient. The clip 10 secures the catheter 48 and prevents the catheter from kinking or otherwise collapsing when subjected to lateral bending forces at the juncture with the connector by spreading the bending forces along an adequate length of the catheter tube displaced from the connector. It should be appreciated, however, that the clip 10 is not limited to any particular use or medical procedure, and is not limited to combination with any other component, such as a catheter connector.

The clip 10 in the illustrated embodiments has a body member 12 with an upper surface 14 and a bottom surface 16. The body 12 can be made of any suitable medical-grade material, and can have any conventional overall shape, such as circular, oval, square, and so forth. In a particular embodiment illustrated in the figures, the body 12 has an overall rectangular shape with a first side 18 and an opposite second side 20.

A plurality of arm members 22 are provided on the body 12, with each arm member 22 extending upwardly from the upper surface 14 so as to define an undercut region 32 between a lower surface of the arm member 22 and a plane of the upper surface 14 of the body 12. The undercut region 32 is configured for receipt of a catheter 48 under the respective arm member 22, as particularly illustrated in FIGS. 4 through 6. In certain embodiments, the catheter may be frictionally engaged against the underside of the arm member 22, or may be freely movable in the undercut region 32.

The arm members 22 may have any shape and size for performing their intended function. In the illustrated embodiments, the arm members 22 have a generally elongated prong-like shape with a rounded free end 24 and an opposite end 26 that is formed, attached, or otherwise connected with the upper surface of the body 12. The arm members 22 may be molded integral with the body 12, and extend at an angle from the upper surface 14 of body 12 to a relatively flat upper surface 25 of the respective arm member. In other embodiments, the arm members 22 may be separately formed and attached to the body member 12.

The arm members 12 are provided in sufficient number and orientation on the upper surface 14 so as to define a bent path for the catheter 48 threaded under each of the arm members 22 from the first side 18 to another side, for example the opposite side 20 of the body 12. This bent path may have any number of configurations. For example, in the illustrated embodiments, three arm members 22 define a bent path having at least two angled segments from the first side 18 to the opposite side 20 of the body 12. Depending on the number and location of the arm members 22, the bent path may be defined to one side of an axis between the outermost arm members 22, as in the illustrated embodiments. In other words, the catheter 48 enters the body 12 at the first side 18, changes direction at each arm member 22 (e.g., three times in the illustrated embodiment), and exits the body 12 at the opposite side 20 in the same direction that it entered at the first side 18, wherein the arm members 22 intermediate of the outermost arm members are all to one side of the axis or line between the outermost arm members 22. This embodiment may be desired to reduce the overall width of the body member while at the same time providing adequate retention and directional change of the catheter 48 for strain relief purposes.

The term "bent path" is used herein to encompass any shaped path wherein the catheter changes direction at least once from one side of the body member to the other side, and includes continuous directional changes such as a curve, segmented directional changes as depicted in the figures, or any other type of directionally changing path.

It should be appreciated that the bent path defined by the arm members 22 may vary widely within the scope and spirit of the invention. For example, in a non-illustrated embodiment, the bent path may be serpentine in that it crosses back and forth relative to an axis between the outermost arm members 22. In other embodiments, the exit of the bent path need not be at the opposite side 20 of the body 12, but may be at an arm member along one of the perpendicular side walls of the body 12.

In a particular embodiment illustrated for example in FIGS. 1 and 2, all of the arm members 22 are oriented parallel to each other on the upper surface 14 of body 12 such that the change in direction of the bent path is due primarily to the offset of the arm members relative to each other (relative to an axis or line between the outermost arm members 22).

In another embodiment depicted for example in FIG. 3, one or more of the arm members 22 may be oriented at non-parallel angles relative to the other arm members such that the change in direction of the bent path is also due to an angular skew between certain of the arm members 22. For example, referring to FIG. 3, the opposite outermost arm members 22 are oriented at a non-parallel angle on the upper surface 14 relative to each other (and relative to the intermediate arm member 22) so as to increase the directional change of the bent path at the sides 18, 20 of the body 12. As can be appreciated from the top view of FIG. 3, the outermost arm members 22 are skewed so to create an increased angle portion of the bent path at the opposite sides 18, 20 of the body as compared to the embodiment of FIGS. 1 and 2.

The arm members 22 may be rigid relative to the upper surface 14 of body 12, or may be resiliently configured on the body 12 so as to flex for insertion and removal of the catheter 48 from the undercut regions 23. Referring to FIGS. 1 and 2, a retention lip 28 may be defined on the underside of each arm member 22 to prevent inadvertent slippage of the catheter 48 from under the arm member 22. The arm members 22 may include an inclined face 30 on the underside thereof extending from the retention lip 28 to the free end 24 to aid with sliding insertion of the catheter under the respective arm member 22.

In the embodiment of FIGS. 1 and 5, a recess or hole 34 is defined partially or completely through the body member 12 at each of the undercut regions 32. This hole 34 defines a space wherein the catheter 48 disposed through the undercut region 32 can deflect vertically into the hole 34, as depicted in FIG. 5.

In the embodiment of FIGS. 2 and 4, the upper surface 14 is generally flat and continuous along the undercut region 32, wherein the catheter 48 lies against the surface 14 below the arm members 22.

As depicted in the various figures, recessed channels function as grooves 36 in the upper surface 14 of the body 12 between each of the arm members 22, wherein the recessed channels or grooves 36 are configured for receipt of the catheter therein between adjacent arm members, as well as at the sides 18, 20. In the illustrated embodiments, end grooves 38 are defined at the sides 18, 20 and provide an entry and exit recessed portion of the bent path. Intermediate grooves 40 can interconnect the arm members 22 and additional recessed portions of the bent path. The grooves 38, 40 shown in figures are defined at one or both of their opposite ends by walls 42 that limit the extent of the groove, with the walls 42 disposed generally adjacent to the undercut regions 32. For example, each arm member 22 may be flanked by such delimiting walls 42. With this configuration, as particularly illustrated in the views of FIGS. 4 and 5, a catheter 48 seated in the grooves 40 is deflected vertically by the walls 42 at each side of the undercut regions 32. In addition, if a recess or hole 34 is defined in the body 12 at the undercut regions 32, as in FIGS. 1 and 5, the catheter is deflected vertically downward into such recess or hole 34 at the undercut regions. The cumulative effect of the various vertical deflections of the catheter 48 is beneficial in retaining the catheter and relieving axial stresses, particularly if the catheter is subjected to a pulling force from only one direction.

The clip device 10 may be provided with various adhesive means to retain the device at a target location on the patient. For example, referring to FIGS. 4 and 5, the underside 16 of the body 12 may be relatively flat and provided with an adhesive layer 44 thereon (which may be protected with a peel-off layer until use of the device 10).

Referring to FIG. 6, an embodiment of the clip 10 in accordance with aspects of the invention may include an attachment pad 46, for example a foam pad, for adhering the clip 10 to a patient, for example directly to the patient's skin 50 adjacent to a catheter insertion site. This pad 46 may be made of any suitable material and may be adhered to the lower surface 16 of the body 12. The grooves in the embodiment of FIG. 6 do not include end walls, which may be desirable in certain situations.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A catheter strain relief clip, comprising:
    a body having an upper surface;
    a plurality of arm members extending upwardly from said upper surface;
    each of said arm members defining a free end and an undercut region on an underside of a flat upper surface for receipt of a catheter;
    wherein said arm members are disposed so as to define a bent path for a catheter threaded under each of said arm members from a first side to a second side of said body; and
    a groove defined in said upper surface between each of said arm members, said grooves defining a recessed channel in said upper surface between adjacent said arm members, said arm members extending over a path for the catheter between adjacent grooves and oriented such that a catheter inserted under said free end of said arm members is disposed in said recessed channels as the catheter runs along the bent path.

2. The catheter strain relief clip as in claim 1, wherein said arm members define a bent path of at least two angled segments from said first side to said second side of said body.

3. The catheter strain relief clip as in claim 2, comprising at least three of said arm members, wherein said bent path is defined to one side of outermost arm members at said first side and said second side of said body.

4. The catheter strain relief clip as in claim 3, wherein said arm members are oriented parallel to each other on said upper surface.

5. The catheter strain relief clip as in claim 3, wherein at least two of said arm members are oriented at non-parallel angles to each other on said upper surface such that the change in direction of the bent path is also due to an angular skew between angled arm members.

6. The catheter strain relief clip as in claim 5, wherein opposite outermost ones of said arm members are oriented at a non-parallel angle on said upper surface so as to create an increased angle portion of the bent path at said first side and said second side of said body.

7. The catheter strain relief clip as in claim 1, wherein said arm members are resiliently configured on said body and flex for insertion of the catheter into said undercut region.

8. The catheter strain relief clip as in claim 7, wherein said arm members comprise a retention lip defined on an underside thereof.

9. The catheter strain relief clip as in claim 8, wherein said arm members comprise a free front end and an inclined face from said front end to said retention lip.

10. The catheter strain relief clip as in claim 1, further comprising a recess or hole in said body at each of said undercut regions, wherein a catheter disposed through said undercut regions can deflect vertically into said recess or hole.

11. The catheter strain relief clip as in claim 1, wherein each of said grooves includes a delimiting wall at ends thereof adjacent a respective said arm member such that each said arm member is flanked by said delimiting walls, said delimiting walls generating a vertical deflection of the catheter from the grooves into the undercut regions.

12. The catheter strain relief clip as in claim 11, further comprising a recess or hole in said body at each of said undercut regions, wherein a catheter disposed through said undercut regions can deflect vertically into said recess or hole.

13. The catheter strain relief clip as in claim 1, wherein said body comprises a flat underside, and further comprising an adhesive on said flat underside for securing said clip at a target location.

14. The catheter strain relief clip as in claim 1, further comprising an attachment pad connected to an underside of said body for securing said clip at a target location.

* * * * *